United States Patent [19]

Bergeron

[11] 4,141,937
[45] Feb. 27, 1979

[54] SOLVENT RECOVERY PROCESS

[75] Inventor: Charles R. Bergeron, Baton Rouge, La.

[73] Assignee: Ethyl Corporation, Richmond, Va.

[21] Appl. No.: 676,858

[22] Filed: Apr. 14, 1976

Related U.S. Application Data

[63] Continuation-in-part of Ser. No. 275,248, Jul. 26, 1972, abandoned.

[51] Int. Cl.$^2$ .......................... C07C 7/02; C07F 9/24
[52] U.S. Cl. ................................. 260/927 N; 203/46
[58] Field of Search .......... 260/927 M, 643 R, 583 N, 260/290 A; 203/46

[56] References Cited

U.S. PATENT DOCUMENTS

| | | | |
|---|---|---|---|
| 3,136,727 | 6/1964 | Nichols | 260/927 N |
| 3,291,865 | 12/1966 | Kober et al. | 260/927 N |
| 3,294,872 | 12/1966 | Allcock | 260/927 N |
| 3,468,981 | 9/1969 | Bezman | 260/927 N |
| 3,794,701 | 2/1974 | Bik | 260/927 N |
| 3,891,448 | 6/1975 | Braxton et al. | 260/927 M |
| 3,974,242 | 8/1976 | Lanier et al. | 260/927 M |

Primary Examiner—Paul M. Coughlan, Jr.
Assistant Examiner—W. B. Springer
Attorney, Agent, or Firm—Donald L. Johnson; John F. Silberth; James M. Pelton

[57] ABSTRACT

A process for the recovery of materials suitable for recycle to the manufacture of alkoxy or aryloxyphosphazenes including, inter alia, solvents, hydroxy compounds, acid acceptors and the like, from flash distillation of the washed phosphazene product together with a second vapor stream produced from the aqueous wash of the crude phosphazene product, whereby an aqueous phase and an organic phase are produced and recyclable materials are extracted from the aqueous phase into the organic phase, separating the organic phase from the aqueous phase and separating the organic phase into components by conventional methods which are suitable recycle streams for the phosphazene product manufacturing process.

10 Claims, 1 Drawing Figure

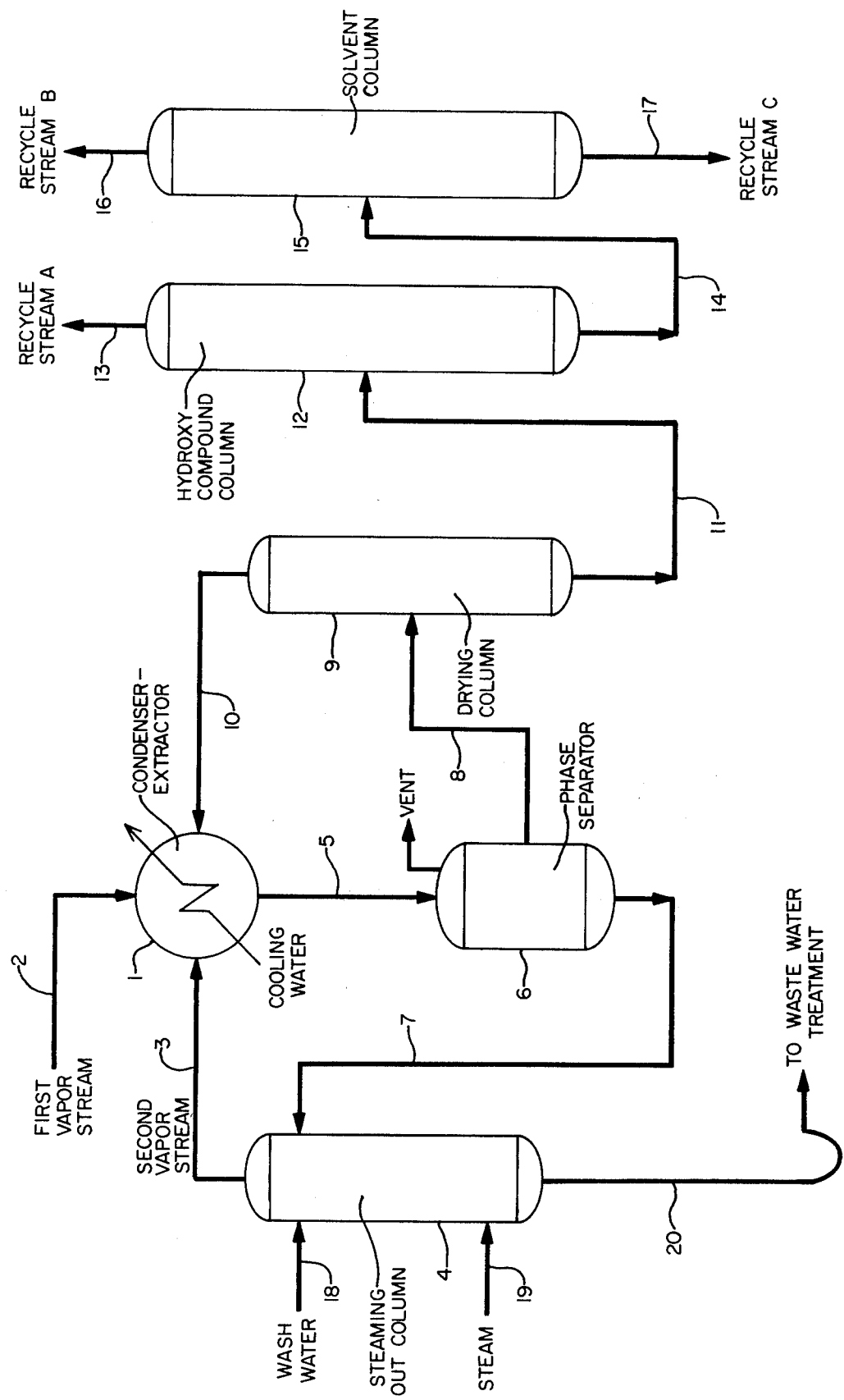

SOLVENT RECOVERY PROCESS

CROSS-REFERENCE TO RELATED APPLICATION

This application is a Continuation-in-Part of application Ser. No. 275,248, filed July 26, 1972, now abandoned.

BACKGROUND OF THE INVENTION

Considerable interest has recently developed in the production of phosphazene compounds (also known as phosphonitrilate ester compounds) as fire retardants for cellulosic materials, as plastics with exceptional solvent and chemical resistance, for treatment of polyesters and as elastomers. Of particular interest is production of alkoxy and aryloxyphosphazenes, especially hexapropoxyphosphazene (HPP). Several methods of preparation of alkoxy and aryloxyphosphazenes are known. In general, the reaction schemes employed include the reaction of a phosphonitrilic chloride with a hydroxy compound or metal alcoholate to produce the desired phosphazene compound. In Stokes, *American Chemical Journal*, Vol. 19, p. 782 (1897) and Schenck et al, Berichte, Vol. 57B, p. 1343 (1924), the formation of phosphonitrilic chlorides by the reaction of phosphorus pentachloride with ammonium chloride is taught. More recently, U.S. Pat. No. 3,656,916 to Schiedermier et al teaches the reaction of ammonia with phosphorus pentachloride to produce phosphonitrilic chlorides. The compounds react with alcohol or the sodium alcoholate prepared by known methods, such as reacting excess alcohol with molten sodium in a suitable solvent, to prepare the desired phosphazene compound.

Further illustrating processes and the types of materials which are suitable for recycle to the manufacture of phosphazene compound are U.S. Pat. No. 3,795,526 to Bergeron in which a condensed cyclic alkoxy or aryloxy phosphazene is produced starting with a phosphonitrilic chloride and a hydroxy compound, such as monohydric aliphatic and aromatic alcohols or the alkali metal derivatives thereof, and an alkali metal hydroxide which aids in the condensation. Solvents employed include aromatic hydrocarbons, such as benzene, toluene, xylene and chlorobenzene; aliphatic hydrocarbons such as heptane; and commercially available mixtures such as kerosene, No. 9 oil, etc. Also unreacted hydroxy compound such as excess propanol must be removed from the product or intermediates therefor. In U.S. Pat. No. 3,836,608 a partially esterified phosphonitrilic chloride, prepared from the reaction of phosphonitrilic chloride and an alcohol or alkoxide, is heated and self-condenses to form a condensed polymeric phosphazene with P-O-P linkages. Solvents used include octane or chlorobenzene. Impurities are removed, such as by filtration and washing. Solvent is removed by heating in vacuo (e.g. 85°, 16 torr) to concentrate the partial ester. However, no mention is made of recovering the solvent or unreacted alcohol. On condensation, an alkyl halide is evolved. There is likewise no mention of recovery of the alkyl halide. In U.S. Pat. No. 3,840,621 an esterified phosphazene is produced by reacting a chlorophosphazene with ethylene glycol or other low molecular weight glycol, and if desired, further esterifying with alcohol, alkoxide, or alkylene oxide. Aromatic and paraffinic solvents are employed and amines, such as triethylamine, are used to complex with the HCl liberated on esterification. Removal of the solvent, amine and unreacted alcohol is required but no method of recovery is suggested. In U.S. Pat. No. 3,844,983, a poly(fluoroalkoxyphosphazene) copolymer is produced by reacting a poly(dichlorophosphazene), an alkali metal salt of an alcohol or a mixture of different alcohol salts, and a third alkali metal salt of an alcohol containing an amine function. Solvents employed include benzene, toluene, xylene, chlorobenzene, 1,2-dichlorobenzene, tetrahydrofuran or mixtures thereof. Washing with water and separation of organic and aqueous phases are mentioned for separation of the poly(fluoroalkoxyphosphazene) prior to curing or crosslinking of the polymer, but no mention is made of the recovery of solvent or excess alcohol for recycle. More recently in application Ser. No. 529,760, filed December 5, 1974, now U.S. Pat. No. 3,974,242 issued Aug. 10, 1976 there is taught a process for reacting a phosphonitrilic halide and an aromatic or aliphatic alcohol in the presence of an acid acceptor, particularly a tertiary amine, whereby a condensed phosphonitrilate ester is produced. Excess alcohol, tertiary amine and process solvent such as chlorobenzene must be recovered.

In each of these processes, the use of solvents plays an important role in the process. The earlier work of Stokes and Schenck et al, supra, used symmetrical tetrachloroethane as a solvent for the preparation of the phosphonitrilic chlorides. However, this material is expensive and very toxic. More recently, emphasis for this reaction has been placed on the use of monochlorobenzene. In addition, the reaction for producing the phosphazene has been carried out in the presence of tertiary amines as an acid acceptor because the reaction liberates large quantities of hydrogen chloride. In more recent studies, the use of toluene has been shown to provide acceptable properties in the alkoxyphosphazene reaction. In many cases, however, the result is a mixed solvent system, unless extensive steps are taken to remove the solvent prior to reaction further with the alcohol or alcoholate.

The use of the mixed solvents, the presence of unreacted alcohol and amine complexes poses practical problems in the production of alkoxy and aryloxyphosphazenes. For commercial application a process must not only provide the desired end-product in good quality and good yield, it must also be considered from an economical standpoint in the recovery and reuse of the auxiliary materials such as solvent and unreacted alcohol. The nature of the mixed solvent system provides difficulty in separation especially when it is considered that the solvents must be separated from an aqueous wash system used in purifying the desired phosphazene compound. Previously, it was suggested that extensive liquid-liquid extraction systems requiring large capital expenditures and high processing cost could be used to separate and recover the solvents for recycle to the manufacturing operation. One such system involving the separation and recovery of monochlorobenzene and pyridine is taught in Netherlands Patent Publication 71/06772.

Now a relatively simple and low cost process for recovering solvents, hydroxy compound and tertiary amine acid acceptor suitable for recycle to the manufacture of alkoxy and aryloxyphosphazenes has been found. The present invention allows good solvent separations, provides for low losses of useful materials and, in addition, avoids the use of an elaborate extraction system for separation of organic materials from the aqueous wash system.

It is an object of this invention to provide a process for the recovery of solvent, hydroxy compound and tertiary amine acid acceptor in the manufacture of alkoxy and aryloxyphosphazenes. A further object is to provide a more economical process for the manufacture of alkoxy and aryloxyphosphazenes by recovery and recycle of auxiliary materials. In particular, an object is to provide a process for the manufacture of hexapropoxyphosphazene which does not require an elaborate extraction system to recover valuable organic materials from the aqueous wash stream. These and other objects will become apparent from the following description of the invention.

SUMMARY OF THE INVENTION

This invention provides a process for the recovery of materials including solvents, hydroxy compounds and tertiary amine acid acceptors suitable for recycle to a process for manufacturing phosphazene compounds, said solvents being selected from saturated aliphatic hydrocarbyl compounds having from 6 to about 9 carbon atoms and chlorine or bromine substituted aromatic compounds having from 6 to about 10 carbon atoms, said hydroxy compounds being selected from lower aliphatic alcohols, chlorine or bromine substituted lower aliphatic alcohols, aromatic alcohols having from 6 to about 12 carbon atoms, and chlorine or bromine substituted aromatic alcohols having from 6 to about 12 carbon atoms, and said tertiary amine acid acceptors being selected from trimethylamine, triethylamine and pyridine, said process comprising the steps of (a) contacting a first vapor stream containing said solvent and/or said tertiary amine acid acceptor with a second vapor stream containing water and said hydroxy compound in heat exchange relation with a cooling medium whereby said first and said second vapor streams are condensed with the formation of an organic phase and an aqueous phase with the simultaneous extraction of a substantial portion of said hydroxy compound into said organic phase, and (b) separating said organic phase for recovery and recycle to the manufacture of phosphazene (phosphonitrilate ester) compound of said solvent, said hydroxy compounds and said tertiary amine acid acceptor.

In a preferred aspect of the invention there is provided a process for the recovery of monochlorobenzene, heptane and propanol in the manufacture of hexapropoxyphosphazene, said process comprising the steps of:

(a) admixing in heat exchange relation with a cooling medium, a first vapor stream from the flash distillation of washed hexapropoxyphosphazene containing in major proportion monochlorobenzene and heptane with a second vapor stream containing water and propanol, said second vapor stream being produced by vaporizing the wash water from the washing of the crude hexapropoxyphosphazene before the flash distillation whereby said first vapor stream and said second vapor stream are condensed together forming an aqueous phase and an organic phase and a substantial portion of said propanol is extracted into said organic phase;

(b) separating the aqueous and organic phases formed; and (c) heating the organic phase whereby the monochlorobenzene, propanol and heptane are fractionally distilled to produce a propanol-rich heptane fraction, a fraction containing substantially pure heptane and a substantially pure monochlorobenzene fraction.

In another preferred aspect of this invention there is provided a process for the recovery of monochlorobenzene, propanol and pyridine suitable for recycle to a process for manufacturing phosphazene compounds, said process comprising the steps of:

(a) admixing in heat exchange relation with a cooling medium a first vapor stream containing said monochlorobenzene and said pyridine with a second vapor stream containing water and propanol whereby said first and said second vapor streams are condensed with the formation of an organic phase and an aqueous phase with the simultaneous extraction of a substantial portion of said propanol into said organic phase;

(b) separating the aqueous and organic phase formed; and (c) heating the organic phase whereby monochlorobenzene, pyridine and propanol are fractionally distilled to produce a propanol-rich fraction, a pyridine-rich fraction and a monochlorobenzene fraction.

DESCRIPTION OF THE DRAWING

The figure of the drawing is a schematic representation of the process of this invention showing a condenser-extractor with vapor feed lines thereto from a steaming-out column, from a flash distillation vessel (not shown), and from a drying column. The condenser-extractor is connected to a phase separator and the aqueous phase is taken off the bottom and recycled to the steaming-out column. The organic phase is taken from the phase separator and goes to a drying column for removal of water from the organic phase and then to two fractionating columns for separating the organic components which are suitable for recycle to the manufacture of phosphazenes.

DESCRIPTION OF PREFERRED EMBODIMENTS

The process of the present invention is useful in the manufacture of phosphazene compounds. As stated hereinabove, phosphazene compounds (also known as esters of phosphonitrile compounds or phosphonitrilate esters) start with a phosphonitrilic halide, preferably chloride, of the general formula

where $x$ can be from 3 to about 1000 or more. The phosphonitrilic halide of the above formula can be in the form of oligomers, such as trimer, tetramer, pentamer, etc., or polymers and can be cyclic, linear or mixtures of these. Further, depending on the degree of oligomerization or polymerization and whether a single component or mixture is considered the phosphonitrilic halide will be a solid or oily liquid. The structure or form of the starting phosphonitrilic halide will govern the structure of the phosphazene produced, unless some other treatment, modification process or conditions are employed to condense, crosslink or deopolymerize the product phosphazene as desired for a particular purpose or application. Although the phosphonitrilic chloride has been mentioned, the chloride can be replaced with other halogens, especially fluorine and bromine, but iodine may not be practical. The type of phosphazene product obtained depends on the reactants employed and the reaction conditions, so that a wide variety of phosphazene products can be produced. An extensive, but certainly not complete, list of various phosphazene compounds is given in Appendix II, *Phosphorus-Nitrogen Compounds*, H. R. Allcock, Academic Press, New York, 1972, which is incorporated by reference as if fully set forth.

On completion of the phosphazene reaction, i.e., the reaction by which the above types of phosphazene compounds are produced, the product phosphazene is generally filtered, washed and stripped of solvent. Such operations produce streams containing valuable materials as referred to above. One such material is a hydroxy compound. Generally, depending on the type of process used to manufacture the phosphazene product, a hydroxy compound or an alkali metal derivative thereof is employed. Usually an excess of the hydroxy compound or alkali metal derivative is used to insure complete reaction of the phosphonitrilic halide. From about 10 to about 20 percent excess hydroxy compound or alkali metal derivative has been used. Thus, recovery of this material for recycle is important for an economical process. Typical of hydroxy compounds which can be recovered by the process of the present invention are the aromatic or aliphatic alcohols or their substituted, especially halogenated, and polyhydroxylated derivatives. Typically, aromatic alcohols such as cresol, benzyl alcohol, xylenol, nophthol, their substituted derivatives, mixtures thereof and the like, are preferred in this process. Particularly preferred is phenol. More preferred are the aliphatic alcohols and especially the saturated lower aliphatic alcohols. By the term "lower aliphatic" is meant a carbon chain having up to about 4 carbon atoms. For example, alcohols such as methanol, ethanol, butanol, their isomers, substituted derivatives, mixtures thereof and the like, are preferred. More particularly preferred is propanol. Also, alcohols having carbon chains higher than 4 carbon atoms may be used, such as pentanol, hexanol, heptanol, octanol, and the like, including their various isomers, substituted derivatives, mixtures thereof, and the like. Likewise, the unsaturated aliphatic alcohols, such as allyl alcohol, crotyl alcohol, beta-allylethyl alcohol, hexenyl alcohol, heptenyl alcohol and higher unsaturated alcohols, their isomers, substituted derivatives and mixtures thereof. Of course, the substituted alcohols should not have reactive substituents which would interfere with the production of the alkoxy or aryloxyphosphazene or cause significant amounts of undesired by-products.

Likewise, large quantities of solvents are used in phosphazene manufacturing processes and must be separated from the product and recovered in sufficiently pure form for recycle. The particular solvent is chosen with a view to its compatibility with the reactants, its boiling point, ease of separation from the product and inertness in the reaction system. The solvent may be a single material or a mixed solvent. Because of the nature of the reaction components, a mixed solvent has advantages over any single solvent system and is preferred. In many cases, an excess of one reactant can serve as a solvent or a portion of a mixed solvent system. For example, excess hydroxy compound can be used as a portion of the solvent system.

As shown in the prior art, organic solvents are preferred. Both aliphatic and aromatic hydrocarbon solvents can be employed. Preferably, the aliphatic hydrocarbon solvent useful in this invention can be a saturated aliphatic hydrocarbon compound such as a saturated aliphatic hydrocarbon compound having from about 6 to about 10 carbon atoms. Also, the aliphatic hydrocarbon compound can be substituted with halogen atoms, such as chlorine or bromine atoms, forming a saturated haloaliphatic hydrocarbon compound. Most preferred of the aliphatic hydrocarbon compounds are hexane, heptane, octane, isooctane, nonane, decane and commercially available mixtures containing these, such as kerosene, No. 9 oil and the like. Heptane is most highly preferred because of its ready availability, low cost and usefulness as a solvent in preparing alkali metal alkoxides from molten alkali metal and alcohol. Aromatic hydrocarbons can also be employed as solvents in the present invention. Particularly, mononuclear aromatic hydrocarbons are preferred. Typical of these are benzene, xylene and toluene. Also halogenated, particularly chlorinated and brominated, aromatic hydrocarbon compounds are well known as solvents in the production of phosphazenes. Especially preferred are aromatic, mononuclear aromatic, and halogen-substituted mononuclear aromatic hydrocarbon compounds having from 6 to about 10 carbon atoms. For example, chlorobenzene, dichlorobenzene, trichlorobenzene, tetrachlorobenzene, bromobenzene, dibromobenzene, tribromobenzene, tetrabromobenzene, chlorobromobenzene, dichlorobromobenzene, chlorodibromobenzene, chloroxylene, chlorotoluene, tetrachloroxylene, tetrabromoxylene and the like can be mentioned as typical of such aromatic solvents. Most preferred is monochlorobenzene because of its availability, boiling point and low cost.

Further, in many processes for phosphazene manufacture a mixed solvent will result. For example, the preparation of alkali metal alkoxide is conveniently carried out in heptane whereas the preparation of phosphonitrilic chloride can be conducted in chlorobenzene. Instead of removing one, or both, solvents to conduct the reaction between the phosphonitrilic chloride and alkoxide, it is more practical to simply contact the two in their respective solvents with the product phosphonitrilate ester being formed in the mixed solvent system. Alternatively, the mixed solvent system can be prepared prior to the phosphonitrilate ester reaction and the phosphonitrilic chloride and alkali metal alkoxide or aryloxide are added thereto.

In addition to hydroxy compound and solvent, many processes disclosed in the prior art employ a tertiary amine as an acid acceptor. In general, such tertiary amines are selected from lower alkyl tertiary amines having up to about 4 carbon atoms in each radical attached to the nitrogen atom and heterocyclic tertiary amine compounds having from 4 to about 10 carbon atoms. For example, trimethylamine, triethylamine, tripropylamine, tributylamine, methylethyl-i-propylamine, pyridine, lutidine, collidine, quinoline, N-methylpyrrole, N-ethylpyrrole, N-methylpyrrolidine, N-methylpiperidine and the like can be mentioned as illustrative of such tertiary amines. Most preferred are triethylamine, trimethylamine and pyridine because of their ability to complex liberated hydrogen halide, availability and relatively low cost.

From the foregoing disclosure one will understand that a preferred process of this invention is one in which the solvent contains at least two organic solvents, one of which is an aromatic solvent and the other of which is an aliphatic solvent, and in which the hydroxy compound used is an aliphatic alcohol. Further, a more preferred embodiment of the invention is one for the recovery of solvent and hydroxy compound used in the manufacture of phosphazene compounds in which the process employs a solvent which is a mixed solvent containing at least two organic solvents in which the first solvent is an aromatic halohydrocarbon and a second solvent is an aliphatic hydrocarbon and in which the hydroxy compound is a lower aliphatic alcohol.

After the alkoxy or aryloxyphosphazene reaction sequence is completed, a series of product purification steps are employed to remove undesirable materials and purify the phosphazene product. As a first step, the crude product containing solvent is washed with water to remove any ammonium chloride which may have carried through unreacted. If metal alcoholates are used in the reaction, the water wash will also remove the by-product metal chlorides product. Any metal alcoholate which remains unreacted will be removed by the water wash since the alcoholate will be converted in the presence of water to water-soluble metal hydroxide and hydroxy compound. Since an excess of hydroxy compound is generally used in the preparation of the metal alcoholate intermediate, the wash water will also contain a considerable amount of this excess hydroxy compound. Additionally, the wash water will contain a small amount of residual solvent. After water washing, the crude alkoxy or aryloxyphosphazene may be distilled at atmospheric conditions by flashing the solvent, tertiary amine, if present, and that portion of unreacted alcohol not removed in the water wash from the phosphazene product. This step serves to vaporize the auxiliary materials which are delivered to the solvent recovery process of this invention. For convenience, this vapor stream will be termed the first vapor stream. One flash distillation step or a series of flash distillations at various pressures and temperatures may be used to remove the solvent. According to this invention, the wash water is then partially vaporized by heating, for example with steam, so as to concentrate the organic materials contained therein, primarily hydroxy compound, in the vapor phase and remove the vapor overhead. This vapor stream is termed, for convenient reference, the second vapor stream.

By combining the first vapor stream with the second vapor stream and condensing the two vapor streams together, a significant portion of the organic materials, including residual solvent and hydroxy compound, are removed from the condensate of the second vapor stream and extracted from the aqueous phase into the organic phase. The aqueous and organic phases formed are separated. The organic material remaining in the aqueous phase which is not extracted can be recovered by returning the aqueous phase to the steaming-out column. As a result, only about one percent of the unreacted hydroxy compound and less than one percent of solvent is lost to waste streams. The organic phase is dried and separated by suitable means, for example, fractional distillation to recover useful components for recycle to the phosphazene manufacturing process. The resultant recovery of unreacted hydroxy compound is significant when it is considered that a 10–20 percent excess thereof above stoichiometric requirements can be used in the process. It is clear that practically all of this hydroxy compound is recovered and recycled. The following is a general description of the process of this invention.

Generally, the invention involves a process for the recovery of solvent, hydroxy compound and tertiary amine suitable for recycle to the manufacture of phosphazene compounds, said process comprising the steps of (a) condensing a first vapor stream containing said solvent and said tertiary amine, if present, said first vapor stream being produced by heating the washed phosphazene compounds at a temperature sufficient to drive off substantially all of said solvent and said tertiary amine, if present, together with a second vapor stream containing water and said hydroxy compound, said second vapor stream being produced by heating the wash water after washing the crude phosphazene compounds, whereby an aqueous phase and an organic phase are formed with a substantial portion of said hydroxy compound being extracted from the condensate of said second vapor stream into said organic phase, and (b) separating said organic phase from said aqueous phase for recovery of hydroxy compound and solvent streams, and tertiary amine, if present, for recycle to the process for manufacture of said phosphazene compounds.

With reference to the Figure of the Drawing, the process of this invention can be described generally as follows: The solvent vapors which can also contain the tertiary amine from flash distillation of alkoxy or aryloxyphosphazene product are fed into the condenser-extractor 1 by means of vapor line 2. Also, a vapor mixture of hydroxy compound and water from steaming-out column 4 is fed into condenser-extractor 1 by means of vapor line 3. Condenser-extractor 1 can be any convenient vessel adapted for heat-exchange relationship whereby a sufficient amount of cooling medium is available to condense the vapors fed into the vessel, for example, a conventional shell-and-tube heat exchanger. The particular configuration is not critical as long as it provides for good mixing of the vapor streams from vapor lines 2 and 3, ease of fluid flow and adequate heat-exchange surface. The cooling medium is not critical and any conventional means may be employed, for example, water. The vapors are substantially completely condensed and are carried by liquid condensate line 5 to phase separator 6. In a preferred configuration, the condenser-extractor 1 may be attached directly to phase separator 6 and feed the condensate directly thereto. The organic and aqueous phases are allowed to separate with the aqueous phase on bottom being returned to steaming-out column 4 through liquid line 7 for recovery of unextracted hydroxy compound which is recycled to condenserextractor 1.

The organic phase containing solvent, hydroxy compound and, if present, tertiary amine and a small amount of water is fed through liquid line 8 to drying column 9 where the organic material is heated to vaporize the water. Substantially complete water removal is required for reuse of the solvents and the organic effluent from drying column 9 is substantially free of water. However, in driving off the water some organic material is also vaporized and carried off with the water vapor. Therefore, overhead vapor from drying column 9 is returned by vapor line 10 to condenser-extractor 1 for recovery of the organic material such as small amounts of solvent, hydroxy compound and, if present, tertiary amine which is vaporized with water. The heating in drying column 9 may be accomplished by conventional means such as a steam heated reboiler (not shown in the drawing).

The substantially water-free mixture of solvent, hydroxy compound, and, if present, tertiary amine is taken from the bottom of drying column 9 through liquid line 11 and the individual components are separated by conventional means. For example, the Figure shows the mixture from liquid line 11 is fed into a series of fractionating columns for recovery of various recycle streams. In hydroxy compounds column 12 the hydroxy compound is taken overhead through vapor line 13 as recycle stream A. The remainder of the organic mixture is taken out the bottom of hydroxy compound column 12 through liquid line 14 and fed into a second fractionating column, the solvent column 15, for distillation. Recycle stream B is removed through vapor line 16 and removal of recycle stream C is through liquid line 17. The overhead recycle streams A and B can be condensed by means not shown and recycled to particular portions of the alkoxy or aryloxyphosphazene manufacturing process. Recycle stream C in liquid form is simply recycled as is.

The steaming-out column 4 serves to provide a vapor stream enriched in hydroxy compound from the water which is used to wash the crude phosphazene-solvent mixture. It operates conventionally by heating the wash water fed in through liquid line 18 near the top of the steaming-out column 4 with steam fed in at the bottom through steam line 19. The waste water is removed from the bottom of steaming-out column 4 through liquid line 20 for disposal. The overhead vapor containing water and hydroxy compound is fed to condenser-extractor 1.

Of necessity, the recycle steams must be designated generally since their actual identities and compositions depend upon the materials included in the first and second vapor streams, that is, their relative solubilities and boiling points, and the size, configuration and operating conditions of the fractionation columns. These factors are not critical to the operation of the present invention since skilled engineers can calculate from available or easily obtainable information the composition of the various recycle streams or find conditions and column configurations to give recycle streams suitable for the manufacture of phosphazene compounds. For the purpose of illustrating the present invention however, several cases are given below stating qualitatively the composition of the various vapor feed streams and recycle streams. For example, in the preparation of hexapropoxyphosphazene using the process disclosed in U.S. Pat. No. 3,795,526, evaporation of the solvent will produce a mixed solvent vapor containing heptane and monochlorobenzene in the first vapor stream and propanol and water with some residual chlorobenzene in the second vapor stream. The recycle streams resulting can include the following: recycle stream A - propanol-heptane mixture; recycle stream B - primarily heptane; and recycle stream C - practically pure monochlorobenzene. In a similar situation for the production of hexaphenoxyphosphazene, the higher boiling point of phenol will call for a different distribution of materials in the recycle streams but otherwise the operation should be similar to the case of propanol. That is, the first vapor stream can include monochlorobenzene and heptane and the second vapor stream will include water, phenol and residual monochlorobenzene. The recycle streams can have the following major constituents: Recycle stream A — primarily haptane; recycle stream B — practically pure monochlorobenzene; recycle stream C — practically pure phenol. Further, in a process for hexapropoxyphosphazene which employs propanol, chlorobenzene and a tertiary amine acid acceptor, such as trimethylamine, the recycle streams have the following as major constituents: Recycle stream A — trimethylamine; recycle stream B — propanol; recycle stream C — chlorobenzene. Similarily in a process using pyridine as the tertiary amine, with other components being as immediately preceding, the recycle streams have the following as major components: Recycle stream A — propanol; recycle stream B — pyridine; recycle stream C — chlorobenzene. Thus, the recovery process of the present invention has a wide variety of combinations which skilled engineers will readily recognize as practical with the various components being removed from the process at differing points depending generally on their relative boiling points.

One skilled in the chemical process industry can readily understand the advantages of the above described process. The use of appropriate controls, pumps, heating means, condensing means and valving to maintain liquid levels, hold temperatures and pressures and transport the fluids is well within the skill of the art and need not be detailed in this process description for adequate understanding of the invention.

From the foregoing description of the invention, it is clear that a preferred process is one which includes separating the aqueous phase and the organic phase and then heating the organic phase to a temperature sufficient to vaporize substantially all the water remaining in the organic phase, but not sufficient to distill substantial amounts of the organic components, delivering the overhead vapors to the condensation-extraction step for recovery of organic components, and delivering a substantially water-free organic phase to the fractional distillation steps. Similarly, another preferred process of this invention includes the process in which the aqueous phase containing a small amount of unextracted hydroxy compound is steam distilled with the wash water producing the second vapor stream whereby the unextracted hydroxy compound is returned to the condensation-extraction step for recovery thereof. Of course, any residual organic materials remaining in the aqueous phase will be subsequently recovered by return to the steamingout column, vaporization and recycle to the condensation-extraction step.

The amount of hydroxy compound remaining unextracted in the aqueous phase is relatively small. This small amount is not critical because the recycle of the aqueous phase to the steamingout columns allows recovery of this unextracted hydroxy compound. Usually, the aqueous phase will contain not less than about 5 weight percent of the hydroxy compound, and preferably from about 7 to about 15 weight percent of hydroxy compound.

The operation of this process for recovery of solvent and hydroxy compound was illustrated by performing experiments to obtain data on the condensation-extraction step. This information enabled calculations to be made to determine the composition of the various product, i.e., recycle, streams from the distillation of the organic phase.

A mixture of n-propanol, monochlorobenzene, n-heptane and water was shaken in a flask to thoroughly disperse the materials. On settling, separate aqueous and organic phases formed. The composition of each phase was analyzed with the following results:

|  | Organic Phase (grams) | Aqueous Phase (grams) |
|---|---|---|
| n-Propanol | 37.0 | 2.7 |
| Monochlorobenzene | 178.0 | 0.004 |
| n-Heptane | 161.0 | <0.004 |
| Water | 2.3 | 16.9 |

The relative quantities of the solvents, alcohol and water shown above represent a practical composition obtained from the manufacture of hexapropoxyphosphazene when the first vapor stream and the second vapor stream are mixed and condensed. Other compositions from solvent vapor and wash water streams may also be obtained, but generally, most practical compositions will not be greatly different. It is important that two phases form in the above mixture and that a reasonable amount of the n-propanol was extracted into the organic phase.

This information, together with binary vapor-liquid equilibrium data available in the literature, was used to calculate the separations which would occur in the phase separator and the distillation columns shown in the Figure of the Drawing. The following stream compositions, in weight percent, were calculated when using distillation columns of practical size, for example, containing about 4 theoretical stages in the steaming-out column and the drying column, and about 20 theoretical stages in the hydroxy compound column and solvent column.

|  | Waste Water (wt %) | Recycle Stream A (wt %) | Recycle Stream B (wt %) | Recycle Stream C (wt %) |
|---|---|---|---|---|
| n-Propanol | 0.6 | 35.0 | 0.13 | <.002 |
| Monochlorobenzene | <.0001 | 0.01 | .004 | 98.0 |
| n-Heptane | <.0001 | 64.1 | 99.9 | 2.0 |
| Water | 99.5 | .0005 | <.0001 | <.0001 |

To one knowledgable in the technology of hexaalkoxy phosphazene production, it is obvious that the above solvent and alcohol streams are of a quality suitable for recycle to the process. For example, the recycled n-propanol can contain appreciable n-heptane since the n-heptane is a suitable solvent in the alcohol-alkali metal reaction to produce the alkali metal propoxide. Note also the very low concentration of water in the solvents; this is important for good results in the phosphazene process. The n-heptane in the monochlorobenzene stream (2%) could be reduced easily by using additional distillation stages in the solvent column, but this is not necessary for good results in the phosphazene process. It is also obvious that the waste water stream contains very little of the valuable organic materials. Notice that the inorganic salts from the phosphazene process which would be present in the water wash are not shown in the above table of data. Since these salts are non-volatile, they will not be present in the overhead vapor from the steaming-out column and therefore have no bearing on the separations of the volatile components.

The operation of the present invention in connection with a phosphazene process described in application Ser. No. 529,760, filed 12/5/74, was illustrated in a manner similar to the previous method by obtaining solubility data on materials in the process streams involved and performing the standard calculations to determine the composition of the streams to be recycled to the phosphazene manufacturing process described above.

A mixture of propanol, monochlorobenzene, propyl chloride, water and pyridine was agitated in a separatory funnel. On settling, an aqueous phase and an organic phase were formed. The phases were separated and analyzed with the following results:

|  | Organic Phase (g) | Aqueous Phase (g) |
|---|---|---|
| Propyl chloride | 4.74 | 0.85 |
| Water | 7.84 | 6.45 |
| Propanol | 6.12 | 0.97 |
| Pyridine | 32.07 | 5.69 |
| Monochlorobenzene | 35.43 | 0.99 |

The relative quantities of the solvent, hydroxy compound, and tertiary amine shown above represent a practical composition obtained from the manufacture of HPP when the first vapor stream and second vapor stream are co-condensed and extracted. Certainly other compositions could be obtained depending on the amounts of solvents, hydroxy compound, tertiary amine, etc., found in the solvent strip and water wash streams, but as stated the above composition of the aqueous and organic phases represent practically obtainable streams suitable for recovery of material for recycle. Again, an important point to note is on contacting and condensing that two phases are formed — an organic phase and an aqueous phase — and that substantial amounts of hydroxy compound are extracted from the aqueous phase into the organic phase.

From the above information, together with binary vaporliquid equilibrium data available in the literature, calculations for separation of the organic phase into various recycle streams by known means, for example distillation, can be made. Referring to the drawing, the following compositions can be expected from the various overhead and bottoms streams based on calculations assuming distillation columns of practical diameter and length. For example, the drying column and steaming-out column was figured using about 7 theoretical stages and the propanol and pyridinemonochlorobenzene columns used about 28 theoretical stages. Such calculations provided the following results on recycle and waste streams:

|  | Waste Water (wt %) | Recycle Stream A (wt %) | Recycle Stream B (wt %) | Recycle Stream C (wt %) |
|---|---|---|---|---|
| Propyl chloride | 0.00 | 0.009 | — | — |
| Water | 99.99 | 135 ppm | — | — |
| n-Propanol | 6.30 ppm | 86.243 | 0.000 | — |
| Pyridine | 0.008 | 10.440 | 98.767 | 0.682 |
| Monochlorobenzene | 0 | 3.306 | 1.231 | 99.318 |
|  | 100 | 100.00 | 99.998 | 100.000 |

To one knowledgeable in the art, it is clear that various changes in the conditions and assumptions can be made in the above calculations to give recycle streams having different compositions. However, the results shown are reasonable and represent practical operational information which clearly illustrate the present invention.

Once the concept of this invention is known, one skilled in the art can determine that the separation scheme shown here can be used equally well when other short chain aliphatic alcohols or aromatic alcohols are used in place of n-propanol in the phosphazene process. For example, phenol, if present in the steaming-out column, will be removed overhead as a low-boiling water azeotrope containing about 10% phenol. Then since the solubility of phenol is greater in paraffinic and aromatic solvents and lower in water than is n-propanol, the condensate of the first vapor stream will extract the phenol from the water in the phase separator. The organic phase from the separator, after drying in the drying column, can then be separated by conventional distillation techniques. In the case of phenol, no azeotrope will form with n-heptane or monochlorobenzene and therefore the phenol will be removed from the bottom of the last column.

In like manner it can be shown that this invention can be used when any short chain aliphatic or simple aromatic alcohol replaces n-propanol in the hexaalkoxy, hexa(haloalkoxy), hexaalkenoxy or hexaryloxy phosphazene process.

From the above description, one skilled in the art will understand that the process of this invention can be varied without departing from the spirit thereof. For example, another preferred process of this invention is a process for the recovery of solvent, hydroxy compound and, if present, tertiary amine suitable for recycle to the manufacture of phosphazene compounds, said process comprising the steps of (a) admixing in heat exchange relation with a cooling medium a first vapor stream containing said solvent and said tertiary amine with a second vapor stream containing water and said hydroxy compound whereby the vapors are condensed forming an aqueous phase and an organic phase with said hydroxy compound, said solvent and said tertiary amine in the organic phase; (b) separating said organic phase from said aqueous phase; (c) heating said organic phase to a temperature sufficient to vaporize substantially all remaining water from said organic phase, and (d) further heating said organic phase to a temperature sufficient to fractionally distill said organic phase which is separated into useful solvent, hydroxy compound and tertiary amine streams for recycle to the manufacture of said phosphazene compounds.

In another aspect of this invention, the process involves separately condensing the first and second vapor streams described hereinabove, mixing the condensate streams formed with suitable agitation whereby an aqueous phase and an organic phase is formed with a substantial portion of the hydroxy compound being extracted into the organic phase. The organic phase is then separated from the aqueous phase and recovering streams suitable for recycle to the manufacture of the phosphazene compounds.

In view of the great flexibility of the process of this invention regarding the type of hydroxy compounds, solvents and tertiary amines which may be recovered, one knowledgeable in the manufacture of phosphazene compounds can envision the application of the present invention to a wide variety of phosphazene compound manufacturing processes. For example, phosphazene processes based on reactions with elemental phosphorus, ammonia and alcohol; or phosphorus pentachloride and ammonium chloride followed by reaction with alcohol or metal alcoholate, and other modifications known in the art can employ this invention.

Therefore, it is to be understood that this invention is not limited to the specific example or process descriptions hereinabove which are illustrative. One skilled in the art will be able to modify the foregoing process without departing from the spirit of the invention.

What is claimed is:

1. A process for the recovery of materials including solvent, hydroxy compound and tertiary amine acid acceptor used in the manufacture of alkyloxy and aryloxyphosphazenes whereby said materials are rendered suitable for recycle to such manufacture, said process comprising the steps of
    (a) contacting a first vapor stream from the distillation of washed alkyloxy or aryloxyphosphazene, said first vapor stream containing solvent composed of (i) heptane and (ii) chlorobenzene and further containing tertiary amine acid acceptor selected from trimethylamine, triethylamine and pyridine, with a second vapor stream produced from the water used to wash said alkyloxy or aryloxyphosphazenes, containing water vapor and hydroxy compound selected from propanol and phenol, in heat exchange relation with a cooling medium whereby said first and said second vapor streams are condensed, forming an organic phase and an aqueous phase with the simultaneous extraction of a substantial portion of said hydroxy compound into said organic phase;
    (b) separating said organic phase from said aqueous phase; and heating said organic phase to a temperature sufficient to vaporize substantially all of the water remaining in the organic phase, but not sufficient to distill substantial amounts of the organic components;
    (c) distilling substantially water free organic phase to produce a stream enriched in said hydroxy compound, a stream enriched in said solvent and a stream enriched in said tertiary amine acid acceptor, and wherein the enriched streams are recycled to the manufacture of said alkyloxy or aryloxyphosphazenes.

2. The process of claim 1 in which said aqueous phase containing a small amount of unextracted hydroxy compound is steam-distilled and returned to said step (a) for recovery of said unextracted hydroxy compound.

3. The process of claim 1 in which said hydroxy compound is propanol.

4. The process of claim 1 in which said hydroxy compound is phenol.

5. The process of claim 1 in which said tertiary amine is trimethylamine.

6. The process of claim 1 in which said tertiary amine is pyridine.

7. The process of claim 1 in which said solvent is a chlorobenzene, said hydroxy compound is propanol, and said tertiary amine is pyridine.

8. A process for the recovery of monochlorobenzene, heptane and propanol used in the manufacture of hexapropoxy phosphazene, said process comprising the steps of
    (a) admixing in heat exchange relation with a cooling medium a first vapor stream from the flash distillation of washed hexapropoxy phosphazene, said first vapor stream containing in major proportions monochlorobenzene and heptane, with a second vapor stream containing water and propanol, said second vapor stream being produced by vaporizing the wash water from the washing of the crude hexapropoxy phosphazene before the flash distillation, whereby said first vapor stream and said second vapor stream are condensed together forming an aqueous and an organic phase with a substantial portion of said propanol being extracted into said organic phase;

(b) separating the aqueous and organic phases formed, and heating said organic phase to a temperature sufficient to vaporize substantially all of the water remaining in the organic phase, but not sufficient to distill substantial amounts of the organic components (c) heating the substantially water free organic phase whereby monochlorobenzene, propanol and heptane are fractionally distilled to produce a propanol-rich heptane fraction, a fraction containing substantially pure heptane, and a substantially pure monochlorobenzene fraction.

9. A process of claim 8 in which said aqueous phase containing a small amount of unextracted propanol is steamdistilled with said wash water producing said second vapor stream whereby said unextracted propanol is returned to the condensation-extraction step (a) for recovery of said unextracted propanol.

10. A process for the recovery of monochlorobenzene, propanol and pyridine used in the manufacture of a propoxyphosphazene product, said process comprising the steps of (a) admixing in heat exchange relation with a cooling medium a first vapor stream from the flash distillation of the washed propoxyphosphazene product, said first vapor stream containing in major proportion monochlorobenzene and pyridine, with a second vapor stream containing water and propanol, said second vapor stream being produced by heating the wash water from washing the crude propoxyphosphazene product, whereby said first vapor stream and said second vapor stream are condensed together forming an aqueous phase and an organic phase with a substantial portion of said propanol being extracted into said organic phase;

(b) separating the aqueous and organic phases; and heating said organic phase to a temperature sufficient to vaporize substantially all of the water remaining in the organic phase, but not sufficient to distill substantial amounts of the organic components;

(c) heating the substantially water free organic phase whereby monochlorobenzene, propanol and pyridine are fractionally distilled to produce a propanol-rich fraction, a pyridine fraction and a substantially pure monochlorobenzene fraction.

* * * * *